United States Patent [19]

Hartley et al.

[11] Patent Number: 4,808,519
[45] Date of Patent: Feb. 28, 1989

[54] METHOD OF DETECTING NUCLEIC ACID SEQUENCES

[75] Inventors: James L. Hartley, Frederick; Mark S. Berninger, Gaithersburg, both of Md.

[73] Assignee: Life Technologies, Inc., Gaithersburg, Md.

[21] Appl. No.: 804,647

[22] PCT Filed: Apr. 6, 1984

[86] PCT No.: PCT/US84/00525
§ 371 Date: Nov. 22, 1985
§ 102(e) Date: Nov. 22, 1985

[87] PCT Pub. No.: WO85/04663
PCT Pub. Date: Oct. 24, 1985

[51] Int. Cl.[4] .................. C12Q 1/68; C07H 21/00; C12N 15/00
[52] U.S. Cl. .................................. 435/6; 935/78; 536/27; 435/803; 435/172.3; 435/29
[58] Field of Search ............ 435/6, 27, 29, 91, 172.3, 435/253, 317, 320, 803; 436/501; 536/27; 935/78

[56] References Cited

U.S. PATENT DOCUMENTS 4,394,443 7/1983 Weissman et al. ............ 435/70 X
4,666,839 5/1987 Souza .............................. 435/68

FOREIGN PATENT DOCUMENTS

WO82/03632 10/1982 PCT Int'l Appl. .

OTHER PUBLICATIONS

Chem. Abst., vol. 104, No. 11, issued Mar. 17, 1986, p. 173, abst. 83081s, Hartley, J. et al., "Detecting Nucleic Acid Sequences".
Supplement European Search Report, (Mar. 2, 1988).

Primary Examiner—Charles F. Warren
Assistant Examiner—Jeremy M. Jay
Attorney, Agent, or Firm—Saidman, Sterne, Kessler & Goldstein

[57] ABSTRACT

A process for detecting specific nucleotide sequences, called targets, in which a special DNA probe molecule, called a probe-vector, is capable of transforming bacteria if and only if it is held in a circular configuration by base pairing to a target nucleic acid, said transformation resulting in the detection of a phenotype specified by the probe-vector, said detection establishing the presence, absence, or quantity of the target; and a probe-vector molecule for performing the process.

27 Claims, 10 Drawing Sheets

METHOD OF DETECTING NUCLEIC ACID SEQUENCES

BACKGROUND OF THE INVENTION

This invention relates to the specific detection of DNA of a specific base sequence. In particular, it relates to the construction of a DNA molecule, termed a "probe-vector", which is complementary to the DNA sequence that one wishes to detect, called the "target" sequence, and which will transform bacteria at high efficiency if and only if it has hybridized with the target sequence.

Deoxyribonucleic acid, or DNA, is a long linear polymer of units called nucleotides. Each nucleotide contains any one of the four nitrogenous bases adenine (A), guanine (G), cytosine (C), and thymine (T). The sequence of bases in an organism's DNA specifies the genetic characteristics of the organism. Most of the individual organisms belonging to a species share most of their respective DNA sequences in common. Accordingly it is possible to identify DNA sequences which all or most of the individual organisms of a species contain but which do not exist in organisms outside the species. Such a DNA is characteristic of the species, and is in a sense "diagnostic" of it.

The ability to detect and identify particular species has application in the diagnosis of infectious diseases. Various pathogens, for example, viruses, bacteria, fungi, and protozoa, can be detected and identified by detecting particular DNA sequence in clinical specimens by this invention. Further genetic characteristics of an infecting organism which affect the pathogenicity or resistance to therapeutic agents (for example antibiotic resistance) can also be detected and identified by this invention.

Within a species, individual organisms exhibit genetic differences from one another. In some cases these differences are manifested as inherited diseases, such as sickle cell anemia in man. These differences can be detected as differences in the base sequence of the DNA of the various organisms. Other diseases such as diabetes and heart disease have genetically determined predispositions which can be identified by characteristic variations in the DNA sequence of the individual. This invention can be applied to detect and identify these variations, and thereby, the genetic predispositions they indicate.

Rearrangements of genomic DNA can result in sequences which were formerly far away from each other being brought into close proximity. Such genetic transpositions occur during development of the immune system, and are implicated in the etiology of some cancers. The probe-vector of this invention requires close linkage between two target sequences for detection of those sequences. Thus suitable probe-vectors can be used to detect rearranged sequences resulting from genetic transpositions.

Since the characteristic DNA sequence one wishes to identify may (is likely to) be found in the presence of a vast abundance of DNA of different sequence it is necessary that its method of detection be highly specific. Further, since little DNA of the characteristic sequence may be available for analysis, a method of high sensitivity is also desirable.

DNA possesses a fundamental property called base complementarity. In nature DNA ordinarily exists in the form of pairs of anti-parallel strands, the bases on each strand projecting from that strand toward the opposite strand. The base adenine (A) on one strand will always be apposed to the base thymine (T) on the other strand, and the base guanine (G) will be apposed to the base cytosine (C). The bases are held in apposition by their ability to hydrogen bond in this specific way. Though each individual bond is relatively weak, the net effect of many adjacent hydrogen bonded bases, together with base stacking effects, is a stable joining of the two complementary strands. These bonds can be broken by treatments such as high pH or high temperature, and these conditions result in the dissociation, or "denaturation", of the two strands. If the DNA is then placed in conditions which make hydrogen bonding of the bases thermodynamically favorable, the DNA strands will anneal, or "hybridize", and reform the original double stranded DNA. If carried out under appropriate conditions, this hybridization can be highly specific. That is, only strands with a high degree of base complementarity will be able to form stable double stranded structures. The relationship of the specificity of hybridization to reaction conditions is well known. Thus hybridization may be used to test whether two pieces of DNA are complementary in their base sequences.

Many genera of bacteria harbor DNA molecules called plasmids. Plasmids are circular molecules which are separate from the main set of bacterial genes. Plasmids can be taken up by bacteria under appropriate conditions, in a process called transformation. They contain the sequences necessary to insure their own replication, and commonly, they also contain other sequences giving the bacteria an easily detectable phenotype, such as antibiotic resistance.

Plasmids have been modified in vitro by a variety of biochemical techniques. Most notable among these are the recombinant DNA procedures whereby sections of foreign DNA are inserted into plasmids. This is accomplished with the aid of various enzymes, in particular restriction endonucleases, which cleave DNA at sites determined by specific base sequences, and ligases, which can be used to re-join the ends of DNA. See U.S. Pat. No. 4,237,224 to Cohen et al.

Of fundamental importance to our invention is the fact that in order to efficiently transform a bacterial cell such as *Escherichia coli*, a plasmid DNA must have a circular configuration. Transformation of *E. coli* with intact double stranded plasmids containing 2-15 kilobase pairs can proceed with an efficiency on the order of $1 \times 10^8$ transformed cells per microgram of input DNA (see D. Hanahan, J. Mol. Biol. 166: 557-580, 1983), or one transformed cell per $10^3$ DNA molecules for plasmids of about 4 kilobase pairs. In contrast, linear plasmid DNA (that is, formerly circular DNA molecules in which both strands have been cut once at the same point) transforms *E. coli* very poorly, perhaps one thousand times less well than the same DNA in a circular form. Plasmids may remain circular even if both strands have been cut, if the cut sites are separated by enough base pairs that the interactions between the strands are strong enough to hold the two cut strands together. Such cut, but still circular, plasmids transform almost as efficiently as uncut molecules (see D. Hanahan, supra).

Circular single stranded DNA molecules exist in nature as the genomes of certain viruses. These DNAs can also enter and establish within *E. coli* cells, but with decreased efficiency (around 1/10th as well as otherwise equivalent double stranded circles). Linear single stranded forms of plasmids transform *E. coli* with efficiencies so low as to be difficult to quantify.

The invention described herein combines the specificity of DNA hybridization with the sensitivity of bacterial transformation to yield a method for the specific and sensitive detection of DNA sequences. An additional benefit of this method is that it is possible, with the appropriate DNA reagents, to clone a portion of the sequence being detected. This permits further study of the DNA by methods such as sequencing and restriction enzyme cleavage.

SUMMARY OF THE INVENTION

According to the present invention, a target DNA sequence is detected by the hydridization of that DNA with a special probe DNA. That special probe, called herein a "probe-vector", is constructed such that it becomes capable of efficiently transforming a bacterial cell—that is, entering a cell and becoming a part of its genetic material—if and only if hybridization with the target has occurred in such a way as to convert the probe-vector from a linear configuration to a circular configuration. A further necessary feature of the probe-vector is that it confers upon transformed cells a heritable detectable phenotype(s) so that the existence of transformed cells may be readily ascertained. With appropriate probe-vectors, a portion of the target may be cloned during the detection assay. Important information may then be obtained by examining these cloned regions.

DETAILED DESCRIPTION OF THE INVENTION

Figure 1:
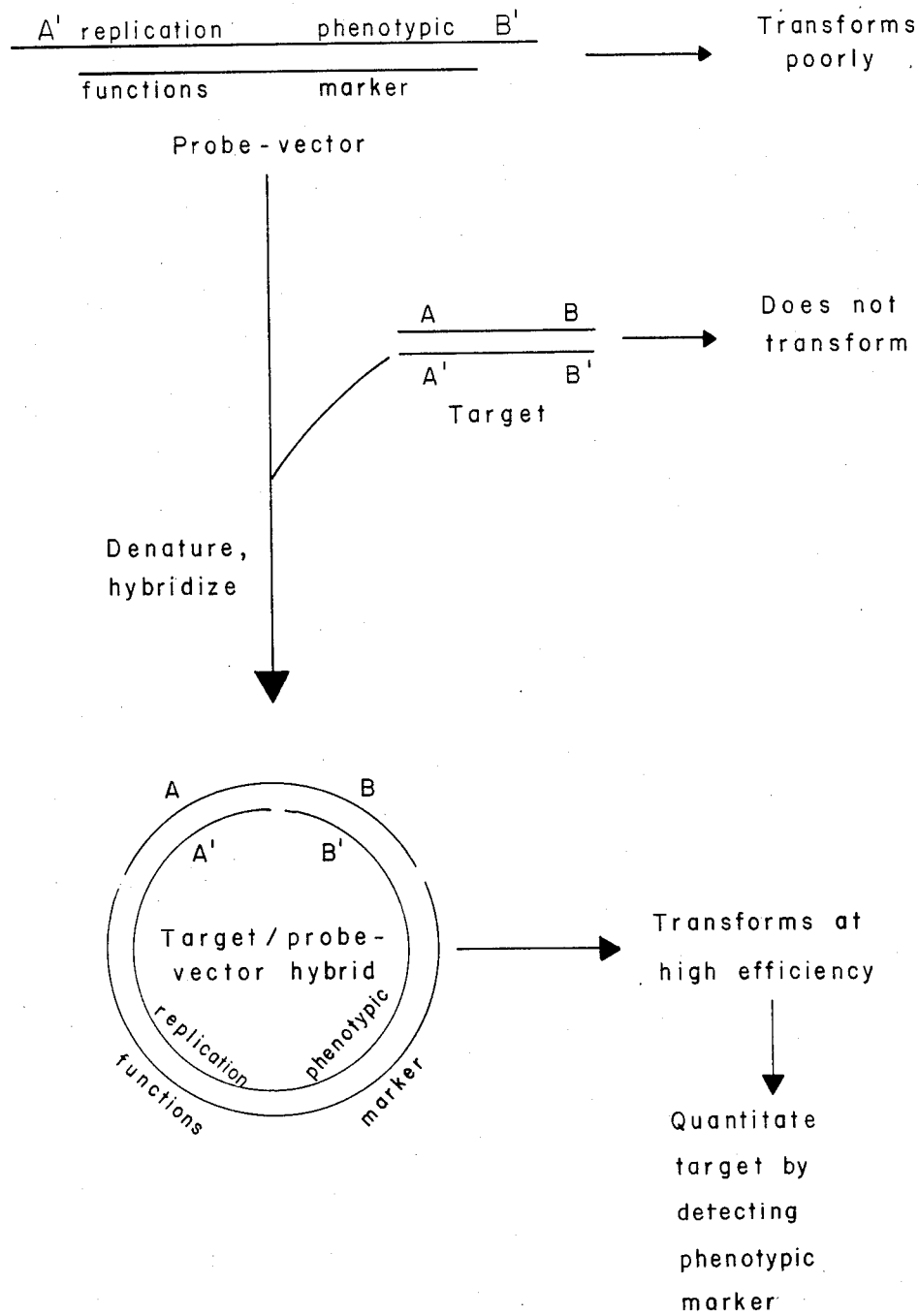
FIG. 1 is a schematic drawing of the detection of a DNA target using a probe-vector according to the invention. The segments A and A', B and B' denote complementary strands and do not imply any biological function.

Referring first to FIG. 1, the probe-vector of our invention is shown as a linear, partially or completely single stranded, derivative of a circular, autonomously replicating DNA molecule, conveniently a plasmid. Base sequences A', B' at the ends of the probe-vector are complementary to portions of the target DNA, and are arranged so that when the probe-vector is mixed with target under hybridizing conditions, the ends of the probe-vector will be hybridized to a single target molecule strand, and the target strand will hold the probe-vector in a circular connfiguration capable of transforming bacteria. In some other region the probe-vector also carries a replicon, which may be of viral or plasmid origin, and the genetic information for a phenotype(s) which allows transformed bacteria to be selected or identified.

In the detection process of FIG. 1, the probe-vector is added to a sample of DNA which may or may not contain the target sequence. After denaturation and hybridization, the mixture is combined with appropriate host bacteria, conveniently *Esherichia coli,* under proper conditions for transformation and under conditions for the selection of the phenotypic marker. If no target is in the sample, the probe is not circularized and few or no transformed cells result. But if the target is present many cells will be transformed. The phenotypic marker permits those cells to be identified. For example the marker may encode resistance to a particular antibiotic to which all the cells are exposed. Only the transformed cells survive and form colonies. When there is a sufficient excess of probe-vector over target DNA, the number of colonies will be a direct function of the amount of target in the sample. Any means of measuring the number of transformants may be used to measure the amount of target DNA in the sample. Potentially useful phenotypes include antibiotic resistance, luminescence, comlementation of nutritional deficiencies, induction or spread of a virus, production of a gene product which can be detected by a colorimetric or fluorescent assay, or combinations of the above.

The virtue of this approach lies in the amplifying effect of the biological system. In the examples cited below, a visible colony containing perhaps ten million bacteria arises from a single event, that is, the entry of a single target/probe-vector hybrid molecule into a single cell. Further, the probe-vector can be constructed so that detection of the target results in cloning a portion of the target. Plasmids isolated from transformed cells contain segments derived only from the target. These segments can be analyzed for features of interest, such as mutations characteristic of certain inherited diseases.

The probe-vector sequences complementary to the target can be large or small, so long as sufficiently stable double stranded hybrids form between the single stranded target and single stranded regions of the probe-vector so as to circularize the probe-vector. In fact, there may be unhybridized regions of the target (without complementary regions present on the probe-vector) extending from the hybrid or within the hybridized regions of the two molecules. Such unhybridized regions of DNA may affect (generally reduce) the efficiency of transformation of the hybridized probe-vector, but these differences are small compared to the difference in transformation efficiency between circular and linear probe-vector, i.e., between probe-vector in the presence and absence of target.

DESCRIPTION OF A PREFERRED EMBODIMENT

The performance of the partially double stranded probe-vector of our invention in transforming bacteria after hybridization is shown by the following experimental example, in which the target sequence was a cloned viral DNA.

EXAMPLE

Figure 2:
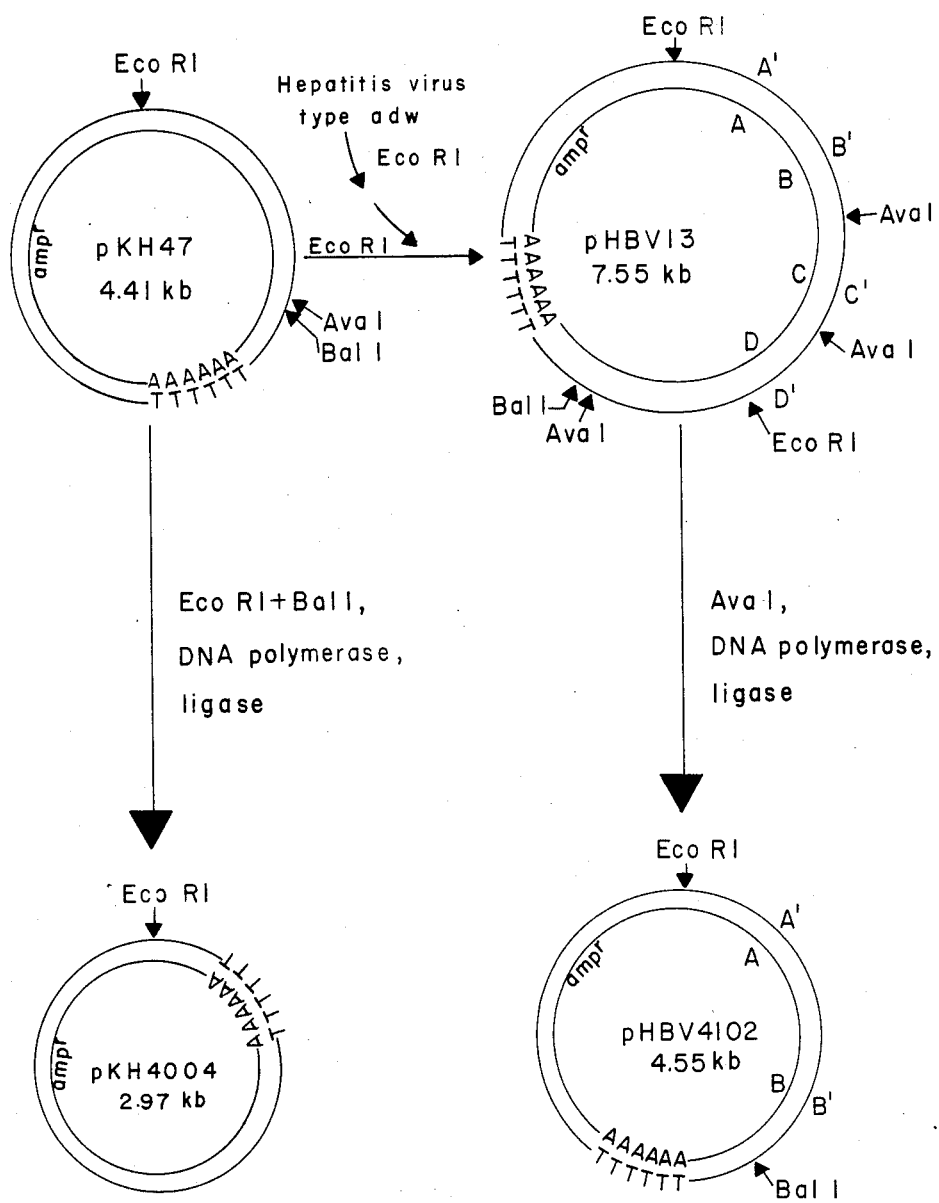
FIG. 2 is a schematic representation of the derivation of plasmids pHBV13, pHBV4102 and pKH4004. The segments A and A', B and B', C and C', D and D' denote complementary strands and do not imply any biological function.
Figure 3:
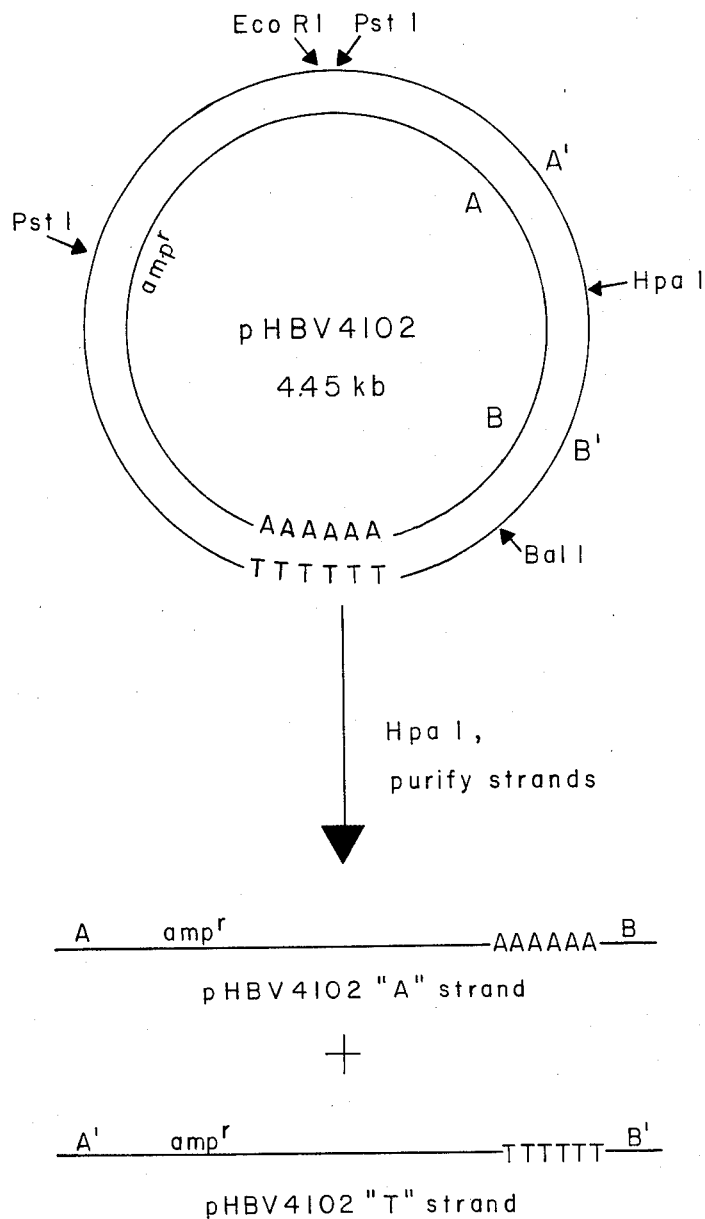
FIGS. 3 and 4 are schematic drawings which illustrate the generation of probe-vector strands from pHBV4102 and pKH4004, respectively.
Figure 4:
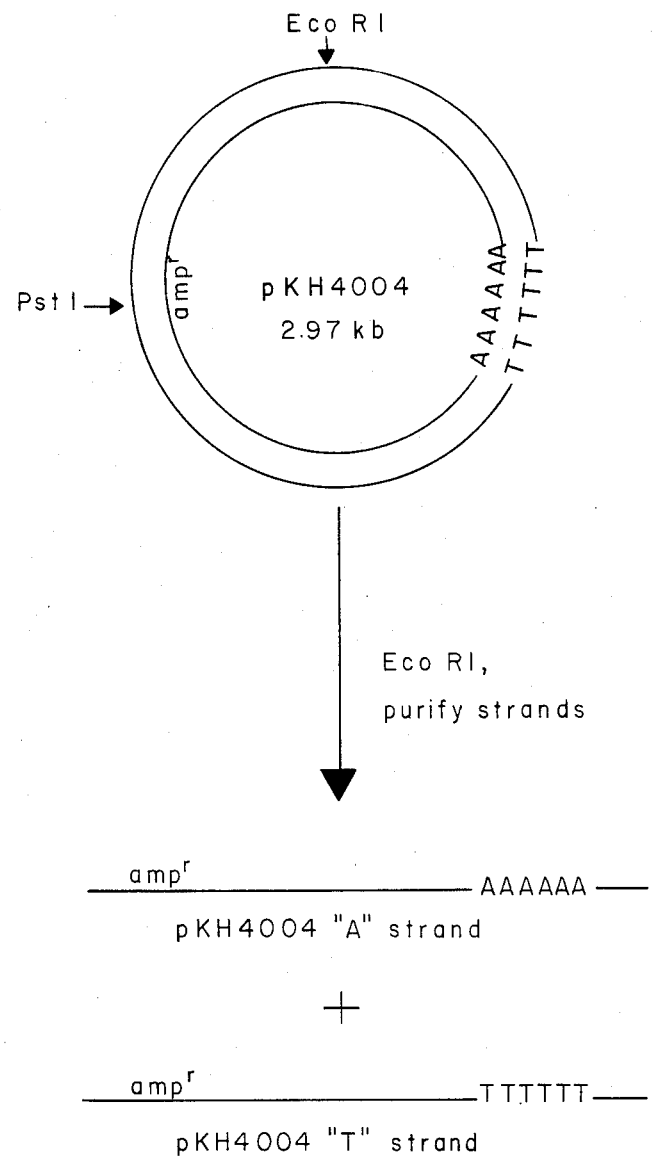
Figure 5:
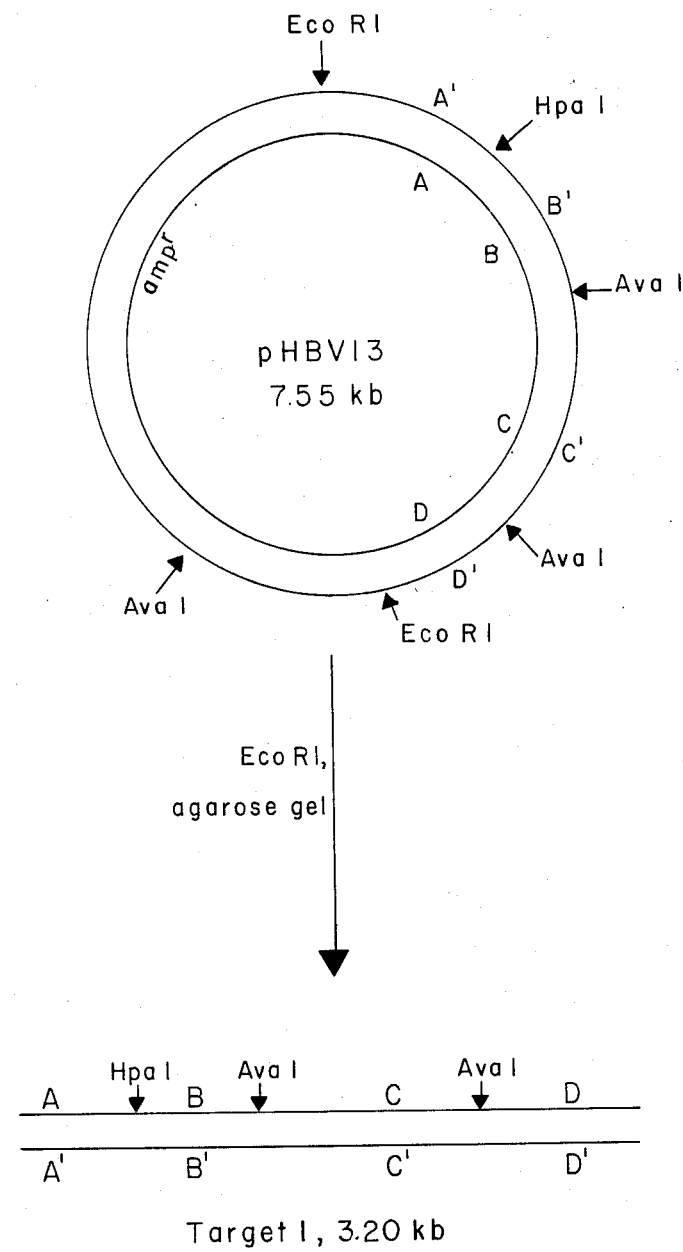
FIG. 5 shows in schematic form the generation of target I hepatitis B virus (HBV) DNA from plasmid pHBV13.

The hepatitis B virus (HBV) genome was cloned into the EcoR I site of the plasmid pKH47 (see K. Hayashi, Gene 11: 109–115, 1980), yielding a plasmid called pHBV13 as shown in FIG. 2. The size of pHBV13 was then reduced by digesting with Ava I, repairing the ends with DNA polymerase I and deoxynucleoside triphosphates, and ligating the ends together, to give pHBV4102. Plasmid pHBV4102 was cut within the hepatitis B region with the enzyme Hpa I, and its "A" strand (containing a long sequence of adenosine nucleosides) was purified by chromatography on oligo-dT cellulose. The plasmid pKH4004 was cut at its EcoR I site, and the "T" strand (containing a long sequence of thymidine nucleosides) was isolated with oligo-dA cellulose. See FIGS. 3 and 4 and Hayashi, supra. When these two strands were mixed under hybridizing conditions, a partially double stranded molecule was formed. Target I for the assay was prepared by digesting pHBV13 with EcoR I and purifying the small fragment, as shown in FIG. 5.

The "T" strand of pKH4004 (8.4 ng) and the "A" strand of pHBV4102 (10.2 ng), each dissolved in water, were mixed in the presence or absence of 25.4 ng of target I (the 3.2 kilobase EcoR I HBV fragment of pHBV13) in a total volume of 6 μl. The reactions were denatured by adding 6 μl of 0.2N NaOH, and then were neutralized by adding 6 μl of a solution comprised of equal volumes of 0.4N HCl and 0.3M Tris HCl pH 8.1. The tubes were incubated for 60 minutes at 65° C., cooled, and half of each reaction was added to E. coli cells which had previously been made competent for transformation. After completion of the transformation protocol, aliquots of cells were spread on agar plates containing nutrients and ampicillin and the plates were incubated overnight at 37° C. The reaction lacking the target gave 13 colonies, while the reaction containing the target gave 2332 colonies (calculated from aliquots).

Figure 6:
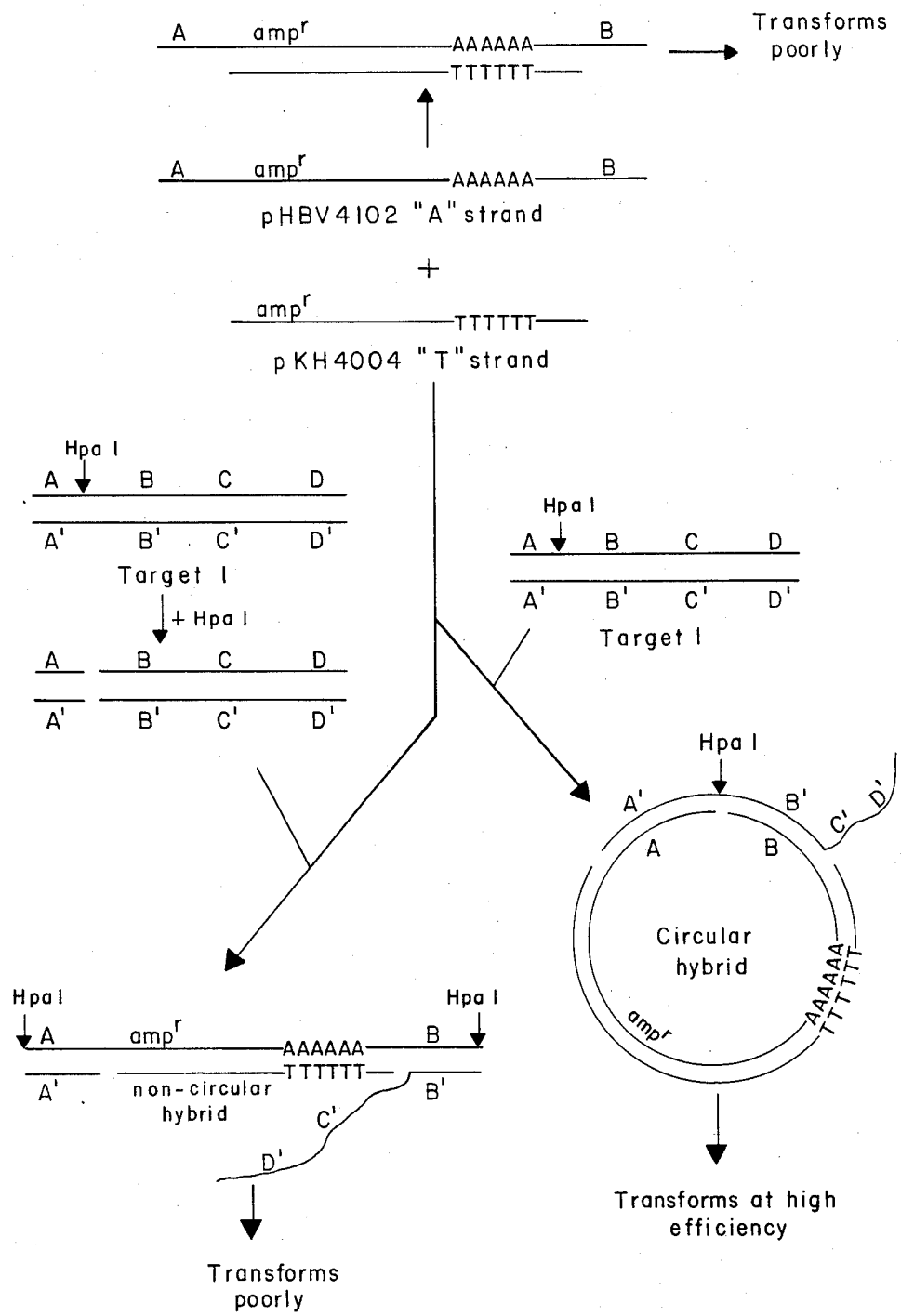
FIG. 6 illustrates the detection of a cloned hepatitis B virus target DNA with a partially double stranded probe-vector. The segments A and A', B and B', C and C', D and D', are complementary to each other do not imply any biological function.

The identical experiment was performed using 23.8 ng of the above target which had been previously digested with Hpa I. this treatment left the target unchanged in its ability to hybridize to the probe-vector, but destroyed its ability to convert the probe-vector to a circular configuration, as shown in FIG. 6. The reaction yielded only 68 colonies, or about 3% of the colonies produced by the identical but uncut target. This result demonstrated the requirement for circularity of the target/prove-vector hybrid for efficient probe-vector transformation.

Note that this result was obtained when the target fragment (3.2 kilobase pairs long) was 1.8 kilobase pairs longer than the complementary regions of the probe-vector. Thus the target/probe-vector hybrid, while circular, contained a long single stranded "tail" of target DNA as illustrated in FIG. 6.

OTHER EXPERIMENTAL EXAMPLES

Single Stranded Probe-vector

In the following experiment the ability of completely single stranded probe-vector to detect a target was demonstrated. Plasmid pHBV4102 was linearized by cutting with Hpa I, and the "T" strand (containing a long sequence of thymidine nucleosides) was purified on oligo-dA cellulose. The "T" strand was digested with Pst I to lower background by digesting any contaminating duplex DNA (single stranded DNA was not digested). HBV target I sequence was prepared from pHBV13 as described above.

Figure 7:
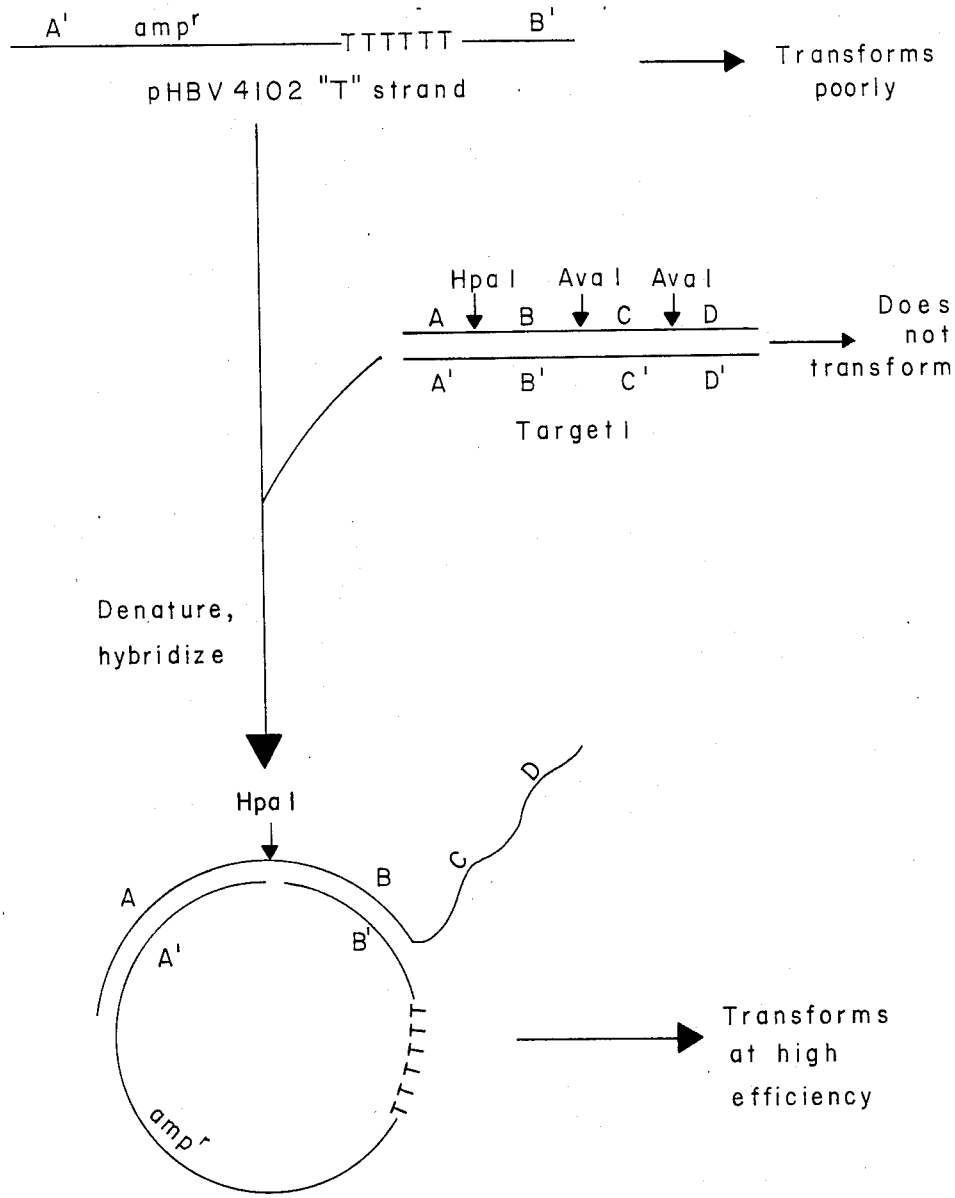
FIG. 7 is a schematic drawing showing the detection of a cloned hepatitis B virus target DNA with a single stranded probe-vector according to an embodiment of the invention.

To detect this cloned HBV target, 3 μl (4.5 ng) of probe-vector "T" strand in 66 mM NaCl, 50 mM Tris HCl pH 8.1, 5 mM MgCl$_2$, were added to 5 μl of 0.16N NaOH containing 12.7 ng of target I. See FIG. 7. Appropriate control reactions were carried through the same protocol. Following denaturation the reactions were neutralized with 4 ∞l of a solution comprised of equal volumes of 0.4N HCl and 0.3M Tris HCl pH 8.1, and incubated at 65° C. for 80 minutes. After chilling the tubes on ice, E. coli cells previously made competent for transformation were added to the reactions and carried through a transformation protocol. Aliquots of cells were spread on agar plates containing nutrients and ampicillin, and incubated overnight at 37° C. The reaction which contained both probe-vector and target yielded 14,888 transformants (calculated from the aliquots), while the negative control reactions (containing either target alone or "T" strand alone) yielded no colonies.

Effect of Non-target DNA on Detection of Hepatitis Target DNA

Plasmid pKH4004 "T" strand (2.1 ng), and pHBV4102 "A" strand (2.5 ng), both prepared as described above, were mixed with 6.2 ng of target I DNA (the EcoR I fragment of pHBV13) which had been digested with Ava I. The target/probe-vector hybrid formed by this combination had virtually no single stranded character and therefore approximated a double stranded plasmid molecule. These DNAs were mixed with different amounts of herring sperm DNA (which should contain no sequences related to hepatitis virus) in a total volume of 3 μl, denatured with 3 μl of 0.2N NaOH, neutralized with 3 μl of a solution composed of equal volumes of 0.4N HCl and 0.3M Tris HCl pH 8.1, and incubated at 65° for 45 minutes. The cooled reactions were used to transform E. coli and yielded the following numbers of transformants:

| ng herring sperm DNA added | colonies (transformants) |
| --- | --- |
| 0, no target | 5 |
| 0, target added | 946 |
| 10, target added | 2178 |
| 100, target added | 957 |
| 1000, target added | 1133 |
| 5000, target added | 2420 |

Thus the addition of a 1000-fold excess of heterologous DNA had no significant effect on the signal (colonies) from the assay. The failure of herring sperm DNA to significantly increase or decrease the yield of transformants indicates that it does not base pair to probe-vector so as to either circularize the probe-vector DNA or prevent the HBV target DNA from circularizing it.

Dose-response Relationship; Detection of Increasing Target

The "T" strand of pKH4004 (2.0 ng) and the "A" strand of pHBV4102 (2.4 ng) were mixed with increasing amounts of HBV target DNA (which had been cut with Ava I, so that the hybrid produced would have no "tail"). These components were taken through denaturation, neutralization, hybridization, and transformation steps similar to those above, and yielded the following results:

| picograms target | colonies (transformants) |
| --- | --- |
| 0 | 7 |
| 4 | 9 |
| 20 | 36 |
| 100 | 88 |
| 500 | 383 |
| 2500 | 1540 |
| 12500 | 3784 |

The signal corresponds directly to the amount of target in the assay.

Detection with Shortened Probe-vector Molecules; Cloning while Detecting

Probe-vector was made by the procedure described below, and the resulting partially double stranded molecule lacked 1419 base pairs from the HBV region. When hybridized to HBV target DNA, the probe-vector was held in a circular configuration, but the two ends of the probe-vector were 1419 bases apart, instead of being precisely juxtaposed as in the previous examples. This type of target/probe-vector hybrid was able to transform E. coli at high efficiency, and plasmids extracted from transformed E. coli cells contained the 1419 base pairs derived only from target DNA.

Figure 8:
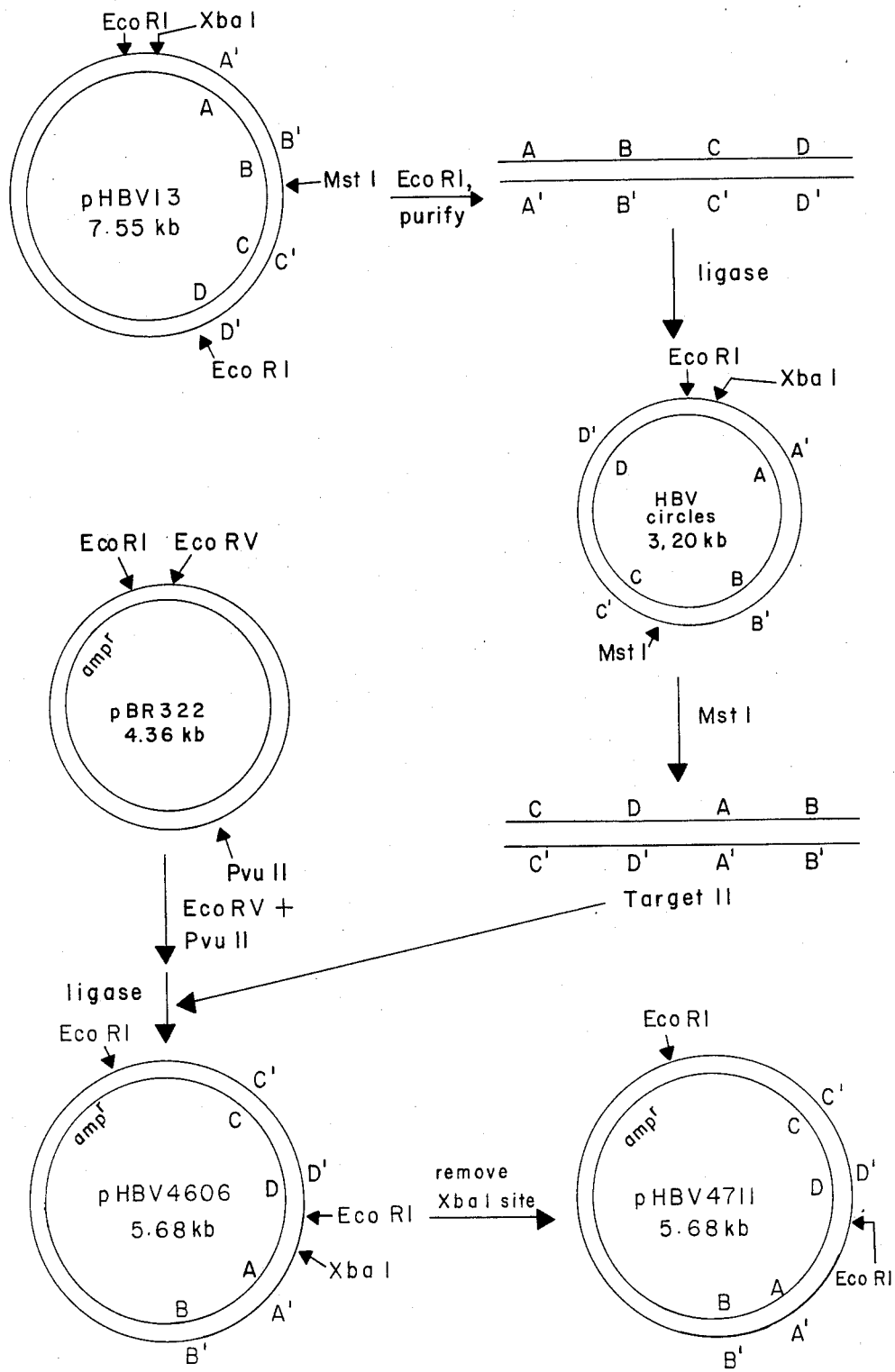
FIG. 8 shows schematically the derivation of plasmid pHBV4711, in which the HBV insert has been cloned in a different arrangement, and the Xba I site has been removed.

Plasmid pHBV4711, whose derivation is shown in FIG. 8, was digested with EcoR V. Deoxynucleoside thiotriphosphates (S-dNTPs, analogs of the noraml deoxynucleoside triphosphates in which one of the oxygen atoms at the alpha phosphate was replaced by a sulfur atom) were incorporated into the 3' ends of the DNA strands by incubating the linear molecule for 5 minutes at 37° C., then 20 minutes on ice, at 0.25 mg DNA/ml in the following reaction mixture: 33 mM Tris acetate pH 7.9, 66 mM potassium acetate, 10 mM Mg acetate, 0.5 mM dithiothreitol, 0.1 mg/ml bovine serum albumin, 2.5 mM each S-dA, S-dG, S-dC, and S-dT (purchased from P-L Biochemicals), and 250 units/ml T4 DNA polymerase. Preliminary experiments showed DNA treated in this way became resistant to the 3'→5' exonuclease activity of exonuclease III, by virtue of the thionucleotides which were incorporated into their 3' ends (see S. D. Putney, et al., Proc. Natl. Acad. Sci. USA 78: 7350-7354, 1981).

Figure 9:
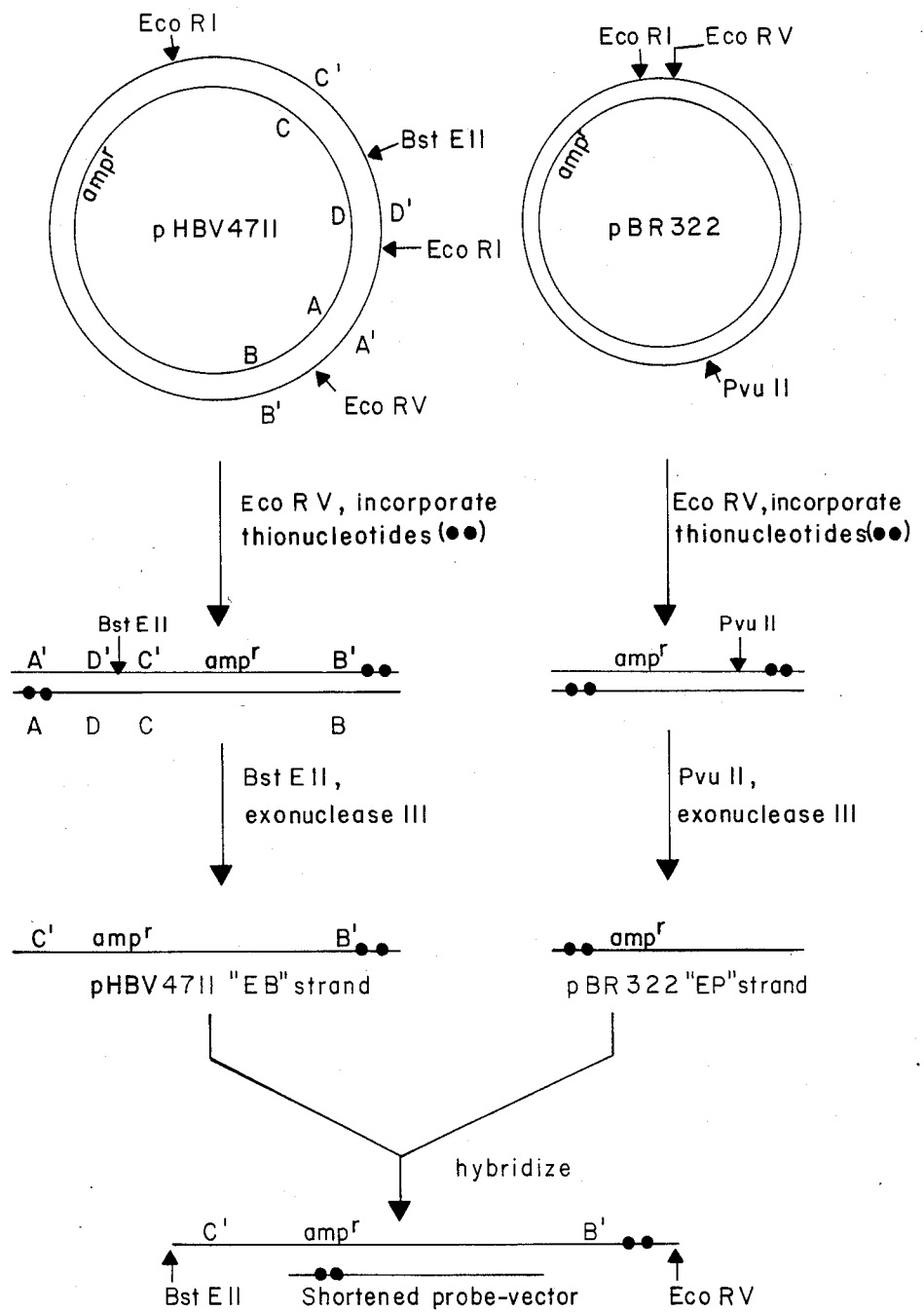
FIG. 9 is a schematic drawing showing the generation of strands from pHBV4711 and pBR322, and their hybridization to form a shortened probe-vector.
Figure 10:
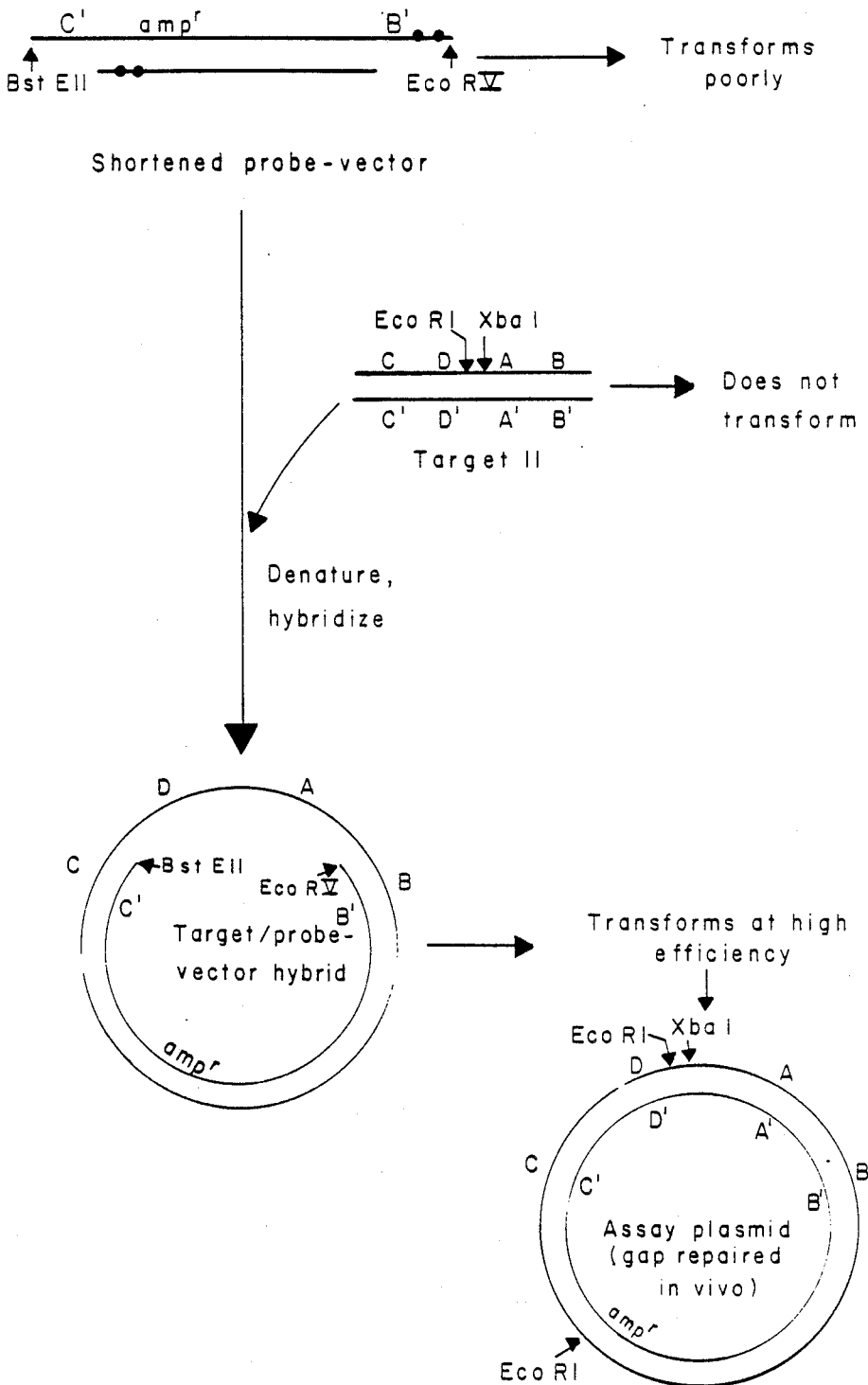
FIG. 10 shows schematically the detection and cloning of HBV target DNA using a shortened probe-vector which lacks a portion of the target sequence.

The protection reaction was phenol extracted, ethanol precipitated, and cut with BstE II, which exposed two unprotected 3' ends. After the BstE II digestion the DNA was phenol extracted and applied to a Sephadex G-50 column. Fractions containing DNA were pooled, ethanol precipitated, and the DNA was dissolved at 0.25 mg/ml in 50 mM Tris HCl pH 7.5, 10 mM MgCl$_2$, 5 mM 2-mercaptoethanol. To this mixture were added 10 units exonuclease III per µg DNA. AFter 30 minutes at 37° C., the reaction mixture was applied to a preparative low melting point agrose gel, and the 4263 base pHBV4711 "EB" strand was purified, as shown in FIG. 9.

To make the opposite strand of the shortened probe-vector plasmid pBR322 was cut with EcoR V, protected from exonuclease III by the incorporation of thionucleotides as above, then cut with Pvu II. Following exonculease III digestion, the 2482 base pBR322 "EP" strand was purified by preparative agarose gel electrophoresis. See FIG. 9.

When 1.4 ng (1 femtomol) of the pHBV4711 "EB" strand and 0.8 ng (1 fmol) of pBR322 "EP" strand were used to detect 0.5 ng of target II (Mst I cut HBV circles), 1429 colonies ("assay colonies") resulted. In the absence of target, 12 background colonies were seen. Target II alone without any strands yielded no colonies. Plasmids from 16 of the assay colonies and 8 of the background colonies were prepared. All 16 of the assay colony plasmids were indistinguishable in size from pHBV4711, as expected if the target/probe-vector hybrid was accurately repaired in vivo. All 8 background plasmids were considerably smaller than pHBV4711. An explanation consistent with these data is that the 1419 base gap between the 5' BstE II end and the 3' EcoR V end of the probe-vector in the target/probe-vector hybrid was repaired in vivo by the E. coli cells, using the hybridized target strand as a template. When 10 randomly chosen assay plasmids were analyzed, expected EcoR I and Xba I sites were confirmed in the gap region of all 10 plasmids. Since the Xba I site was absent from the plasmid from which the strands were made (pHBV4711), but was present in the target, its presence is strong evidence that this region of the assay plasmids was derived from target DNA.

In effect, this region of the target has been cloned during the detection process. This ability to both detect and clone a nucleic acid sequence is likely to have value in the diagnosis of genetic defects in humans. For example, following detection of the beta globin gene with a probe lacking the sickle cell mutation site, plasmid DNA could be isolated from the assay colonies. The presence of the sickle cell mutation (in this case, the presence or absence of a restriction enzyme site) could then be assessed.

The invention has been described in detail with particular emphasis on the preferred embodiments, but it should be understood that variations and modifications within the spirit and scope of the invention may occur to those skilled in the art to which the invention pertains.

We claim:

1. A probe-vector molecule used for detecting a target nucleic acid containing a particular base sequence $X_1X_2X_3 \ldots X_m \ldots Y_1Y_2Y_3 \ldots Y_n$, said probe-vector comprising
   a linear partially single stranded DNA molecule comprised of two strands, a long strand containing the sequence $X'_mX'_{m-1} \ldots X'_3X'_2X'_1 \ldots Z'_1Z'_2Z'_3 \ldots Z'_{hd p} \ldots Y'_nY'_{n-1} \ldots Y'_3Y'_2Y'_1$, and a short strand containing the sequence $Z_1Z_2Z_3 \ldots Z_p$, wherein m, n, p and k are integers, and in which
   for any k, $X'_k$ is the base complementary to $X_k$ is the base complementary to $Y_k$, and $Z'_k$ is the base complementary to $Z_K$, the ends of said long strand of said probe-vector being substantially complementary to sections of said target nucleic acid,
   m and n are sufficiently large so that when said probe-vector is added to said target nucleic acid under hybridizing conditions, stable hybridization will occur between the ends of said long strand of said probe-vector and the said substantially complementary section of said target nucleic acid forming thereby a circular hybrid, the probe-vector being circularized if the particular target sequence is present and has hybridized to said probe-vector, and the regions $Z_1Z_2Z_3 \ldots Z_p$ and $Z'_1Z'_2Z'_3 \ldots Z'_p$ of said probe-vector strands contain a replicon and confer a detectable phenotype such that bacteria transformed by said hybrid are detectable and distinguishable from untransformed bacteria by detection of said phenotype.

2. The probe-vector molecule of claim 1 in which the segments $X'_mX'_{m-1} \ldots X'_3X'_2X'_1$ and $Y'_nY'_{n-1} \ldots Y'_3Y'_2Y'_1$ of the probe-vector are substantially complementary to target regions $X_1X_2X_3 \ldots X_{m-1}X_m$ and $Y_1Y_2Y_3 \ldots Y'_{n-1}Y'_n$, said target regions being non-contiguous and separated by a segment $W_1W_2W_3 \ldots W_q$, where q is an integer such that in the circular hybrid the ends of the long strand of said probe-vector are separated from each other by not hyridizing with the target nuclei acid segment $W_1W_2W_3 \ldots W_q$.

3. A method for determining the presence, in a mixture of DNA, of a target nucleic acid containing a particular base sequence $X_1X_2X_3 \ldots X_m \ldots Y_1Y_2Y_3 \ldots Y_n$, said method requiring the use of a probe-vector having a long strand and a short strand or just a long strand, wherein the long strand comprises the sequence $X'_mX'_{m-1} \ldots X'_3X'_2X'_1 \ldots Z'_1Z'_2Z'_3 \ldots Z'_p \ldots Y'_nY'_{n-1} \ldots Y'_3Y'_2Y'_1$, and the short strand comprises the sequence $Z_1Z_2Z_3 \ldots Z_p$, where m, n, p and k are integers and wherein for any k, $X'_k$ is the base complementary to $X_k$, $Y'_k$ is the base complementary to $Y_k$, and $Z'_k$ is the base complementary to $Z_k$, the ends of said long strand of said probe-vector being substantially complementary to sections of said target nucleic acid, m and n are sufficiently large so that when said probe-vector is added to said target nucleic acid under hybridizing conditions, stable hybridization will occur between the ends of said long strand of said probe-vector and the said substantially complementary section of said target DNA forming thereby a circular hybrid, the probe-vector being circularized if the particular target sequence is present and has hybridized to said prove-vector, and the regions $Z_1Z_2Z_3 \ldots Z_p$ and $Z'_1Z'_2Z'_3 \ldots Z'_p$ of said probe vector strands contain a replicon and confer a detectable phenotype such that bacteria transformed by said hybrid are detectable and distinguishable from untransformed bacteria by detection of said phenotype, said method comprising the following steps:

(A) introducing said probe-vector to the sample containing nucleic acids, said nucleic acids being single stranded or being made single stranded before or after the addition of probe-vector, said mixture of sample and probe-vector comprising the test mixture;

(B) adjusting the conditions of the test mixture to hybridization conditions, such conditions being favorable for the formation of circular hybrids between said long strand and short strand or only with said long strand together with said target if said target is present in the sample, but such conditions being unfavorable for the formation of hybrids between non-target nucleic acids and probe-vector, the test mixture after hybridization comprising the hybridization mixture;

(C) introducing said hybridization mixture to bacterial cells, said bacterial cells being predisposed to transformation by circular DNA molecules but not by linear DNA molecules, said introduction being made under conditions which allow transformation by said circular hybrid but not by linear probe-vector, said bacterial cells lacking the detectable phenotype conferred by said probe-vector, said mixture of bacterial cells and hybridization mixture comprising the transformation mixture;

(D) adjusting the conditions of the transformation mixture to allow detection of the phenotypic marker, said phenotypic marker being exhibited only by transformed cells, such a mixture comprising the detection mixture; and (E) detecting the phenotypic marker in the detection mixture.

4. The method of claim 3 in which the $X'_mX'_{m-1} \ldots X'_3X'_2X'_1$ and $Y'_nY'_{n-1} \ldots Y'_3Y'_2Y'_1$ segments are substantially complementary to target regions $X_mX_{m-1} \ldots X_3X_2X_1$ and $Y_nY_{n-1} \ldots Y_3Y_2Y_1$, said target regions being non contiguous and separated by a segment $W_1W_2W_3 \ldots W_q$, said method resulting in the detection of the target and also resulting in the cloning of the region $W_1W_2W_3 \ldots W_q$ of the target, said region lacking a complementary region on the probe-vector, wherein q is an integer.

5. The method of claim 3 in which the bacteria are *Escherichia coli* and the region $Z'_1Z'_2Z'_3 \ldots Z'_p$ of the probe-vector contains a replicon which functions in *E. coli* and a phenotypic marker which is detectable in *E. coli*.

6. The method of claim 4 in which the bacteria are *Escherichia coli* and the region $Z'_1Z'_2Z'_3 \ldots Z'_p$ of the probe-vector contains a replicon which functions in *E. coli* and a phenotypic marker which is detectable in *E. coli*.

7. The method of claim 3 in which the region $Z'_1Z'_2Z'_3 \ldots Z'_p$ of the probe-vector contains the replicon of the plasmid pBR322 and the ampicillin resistance gene of the plasmid pBR322.

8. The method of claim 4 in which the region $Z'_1Z'_2Z'_3 \ldots Z'_p$ of the probe-vector contains the replicon of the plasmid pBR322 and the ampicillin resistance gene of the plasmid pBR322.

9. The method of claim 3 in which the conditions of the detection mixture are adjusted by placing the detection mixture on solid agar plates formulated to allow the growth of bacterial cells which have been transformed by the circular hybrid, but which will allow the growth of bacterial cells which have not been transformed by said hybrid, incubating said agar plates under appropriate conditions to effect selection of transformed bacterial cells and determining the number of bacterial colonies on the plates, this number constituting a measure of the amount of target nucleic acid present in the same.

10. The method of claim 4 in which the conditions of the detection mixture are adjusted by placing the detection mixture on solid agar plates formulated to allow the growth of bacterial cells which have been transformed by the circular hybrid, but will not allow the growth of bacterial cells which have not been transformed by said hybrid, incubating said agar plates under appropriate conditions to effect selection of transformed bacterial cells and determining the number of bacterial colonies on the plates, this number constituting a measure of the amount of target nucleic acid present in the sample.

11. The method of claim 7 in which the conditions of the detection mixture are adjusted by placing the detection mixture on solid agar plates formulated to allow the growth of bacterial cells which have been transformed by the circular hybrid, but which will not allow the growth of bacterial cells which have not been transformed by said hybrid, incubating said agar plates under appropriate conditions to effect selection of transformed bacterial cells and determining the number of bacterial colonies on the plates, this number constituting a measure of the amount of target nucleic acid present in the sample.

12. The method of claim 3 in which the conditions of the detection mixture are adjusted by placing the detection mixture on solid agar plates containing the antibiotic ampicillin present in an amount sufficient to allow the growth of bacterial cells which have been transformed by the circular hybrid, but which prevents growth of bacterial cells which have not been transformed by said hybrid, said hybrid containing a gene conferring resistance to ampicillin on bacterial cells harboring the hybrid; incubating said agar plates at a suitable temperature to effect selection of transformed bacterial cells and determining the number of ampicillin resistant colonies, said number constituting a measure of the amount of target nuclei acid present in the sample.

13. The method of claim 4 in which the conditions of the detection mixture are adjusted by placing the detection mixture on solid agar plates containing the antibiotic ampicillin present in an amount sufficient to allow the growth of bacterial cells which have been transformed by the circular hybrid, but which prevents growth of bacterial cells which have not been transformed by said circular hybrid, said hybrid containing a gene conferring resistance to ampicillin on bacterial cells harboring the hybrid; incubating said agar plates at a suitable temperature to effect selection of transformed bacterial cells and determining the number of ampicillin resistant colonies, said number constituting a measure of the amount of target nucleic acid present in the sample.

14. The method of claim 7 in which the conditions of the detection mixture are adjusted by placing the detection mixture on solid agar plates containing the antibiotic ampicillin present in an amount sufficient to allow the growth of bacterial cells which have been transformed by the circular hybrid, but which prevents growth of bacterial cells which have not been transformed by said hybrid, said hybrid containing a gene conferring resistance to ampicillin on bacterial cells harboring the hybrid; incubating said agar plates at a suitable temperature to effect selection of transformed bacterial cells and determining the number of ampicillin resistant colonies, said number constituting a measure of the amount of target nucleic acid present in the sample.

15. The method of claim 9 in which the conditions of the detection mixture are adjusted by placing the detection mixture on solid agar plates containing the antibiotic ampicillin present in an amount sufficient to allow the growth of bacterial cells which have been transformed by the circular hybrid, but which prevents growth of bacterial cells which have not been transformed by said hybrid, said hybrid containing a gene conferring resistance to ampicillin on bacterial cells harboring the hybrid; incubating said agar plates at a suitable temperature to effect selection of transformed bacterial cells and determining the number of ampicillin resistant colonies, said number constituting a measure of the amount of target nucleic acid present in the sample.

16. The method of claim 3 in which the target is viral DNA and in which the regions $X'_m X'_{m-1} \ldots X'_3 X'_2 X'_1$ and $Y'_n Y'_{n-1} \ldots Y'_3 Y'_2 Y'_1$ of the probe-vector are complementary to a region of the viral DNA.

17. The method of claim 3 in which the target is $X'_m X'_{m-1} \ldots X'_3 X'_2 X'_1$ and $Y'_n Y'_{n-1} \ldots Y'_3 Y'_2 Y'_1$ which are complementary to a region of the hepatitis B viral DNA or to the entire hepatitis B viral DNA.

18. The method of claim 3 in which the target is viral DNA and in which the regions $X'_m X'_{m-1} \ldots X'_3 X'_2 X'_1$ and $Y'_n Y'_{n-1} \ldots Y'_3 Y'_2 Y'_1$ of the probe-vector are complementary to a region of the viral DNA.

19. The method of claim 4 in which the target is viral DNA and in which the regions $X'_m X'_{m-1} \ldots X'_3 X'_2 X'_1$ and $Y'_n Y'_{n-1} \ldots Y'_3 Y'_2 Y'_1$ of the probe-vector are complementary to a region of the viral DNA.

20. The method of claim 3 in which the target is hepatitis B DNA and the probe-vector contains regions $X'_m X'_{m-1} \ldots X'_3 X'_2 X'_1$ and $Y'_n Y'_{n-1} \ldots Y'_3 Y'_2 Y'_1$ which are complementary to a region of the hepatitis B viral DNA or to the entire hepatitis B viral DNA.

21. The method of claim 4 in which the target is hepatitis B DNA and prove-vector contains regions $X'_m X'_{M-1} \ldots X'_3 X'_2 X'_1$ and $Y'_n Y'_{N-1} \ldots Y'_3 Y'_2 Y'_1$ which are complementary to a region of the hepatitis B viral DNA or to the entire hepatitis B viral DNA.

22. The method of claim 5 in which the target is viral DNA and in which the regions $X'_m X'_{m-1} \ldots X'_3 X'_2 X'_1$ and $Y'_n Y'_{n-1} \ldots Y'_3 Y'_2 Y'_1$ of the probe-vector are complementary to a region of the viral DNA.

23. The method of claim 7 in which the target is viral DNA and in which the regions $X'_m X'_{m-1} \ldots X'_3 X'_2 X'_1$ and $Y'_n Y'_{n-1} \ldots Y'_3 Y'_2 Y'_1$ of the probe-vector are complementary to a region of the viral DNA.

24. The method of claim 18 in which the target is $X'_m X'_{m-1} \ldots X'_3 X'_2 X'_1$ and $Y_n Y_{n-1} \ldots Y_3 Y_2 Y_1$ which are complementary to a region of the hepatitis B viral DNA or to the entire hepatitis B viral DNA.

25. The method of claim 5 in which the target is hepatitis B DNA anb probe-vector contains regions $X'_m X'_{m-1} \ldots X'_3 X'_2 X'_1$ and $Y'_n Y'_{n-1} \ldots Y'_3 Y'_2 Y'_1$ which are complementary to a region of the hepatitis B viral DNA or to the entire hepatitis B viral DNA.

26. The method of claim 7 in which the target is $X'_m X'_{M-1} \ldots X'_3 X'_2 X'_1$ and $Y'_n Y'_{n-1} \ldots Y'_3 Y'_2 Y'_1$ which are complementary to a region of the hepatitis B viral DNA or to the entire hepatitis B viral DNA.

27. The method of claim 12 in which the target is $X'_m X'_{m-1} \ldots X'_3 X'_2 X'_1$ and $Y'_n Y'_{n-1} \ldots Y'_3 Y'_2 Y'_1$ which are complementary to a region of the hepatitis B viral DNA or to the entire hepatitis B viral DNA.

* * * * *